US008680124B2

(12) United States Patent
Wilhelm et al.

(10) Patent No.: US 8,680,124 B2
(45) Date of Patent: Mar. 25, 2014

(54) TREATMENT OF CANCERS WITH ACQUIRED RESISTANCE TO KIT INHIBITORS

(75) Inventors: Scott Wilhelm, Morristown, NJ (US); Richard W. Gedrich, Louisville, CO (US)

(73) Assignee: Bayer Healthcare LLC, Whippany, NJ (US)

( * ) Notice: Subject to any disclaimer, the term of this patent is extended or adjusted under 35 U.S.C. 154(b) by 184 days.

(21) Appl. No.: 12/523,652

(22) PCT Filed: Jan. 18, 2008

(86) PCT No.: PCT/US2008/051406
§ 371 (c)(1),
(2), (4) Date: Jun. 16, 2010

(87) PCT Pub. No.: WO2008/089389
PCT Pub. Date: Jul. 24, 2008

(65) Prior Publication Data
US 2010/0267777 A1 Oct. 21, 2010

Related U.S. Application Data

(60) Provisional application No. 60/885,728, filed on Jan. 19, 2007.

(51) Int. Cl.
A61K 31/4412 (2006.01)
A61P 35/00 (2006.01)
(52) U.S. Cl.
USPC .......................................................... 514/350
(58) Field of Classification Search
USPC .......................................................... 514/350
See application file for complete search history.

(56) References Cited

U.S. PATENT DOCUMENTS

| 7,235,576 | B1 | 6/2007 | Riedl et al. |
| 7,351,834 | B1 | 4/2008 | Riedl et al. |
| 7,517,880 | B2 | 4/2009 | Miller et al. |
| 7,838,541 | B2 | 11/2010 | Dumas et al. |
| 7,897,623 | B2 | 3/2011 | Riedl et al. |
| 8,076,488 | B2 | 12/2011 | Dumas et al. |
| 8,110,587 | B2 | 2/2012 | Dumas et al. |
| 8,124,630 | B2 | 2/2012 | Riedl et al. |
| 2003/0125359 | A1 | 7/2003 | Lyons et al. |
| 2005/0059703 | A1 | 3/2005 | Wilhelm et al. |
| 2006/0019280 | A1 | 1/2006 | Chen et al. |
| 2008/0032979 | A1 | 2/2008 | Riedl et al. |
| 2008/0045589 | A1 | 2/2008 | Kelley |
| 2008/0153823 | A1 | 6/2008 | Riedl et al. |
| 2008/0227828 | A1 | 9/2008 | Dumas et al. |
| 2008/0242707 | A1 | 10/2008 | Schuckler et al. |
| 2009/0093526 | A1 | 4/2009 | Miller et al. |
| 2009/0176791 | A1 | 7/2009 | Sandner et al. |
| 2009/0192127 | A1 | 7/2009 | Scheuring et al. |
| 2009/0306020 | A1 | 12/2009 | Scheuring et al. |
| 2010/0063112 | A1 | 3/2010 | Grunenberg et al. |
| 2010/0113533 | A1 | 5/2010 | Stiehl et al. |
| 2010/0144749 | A1 | 6/2010 | Wilhelm |
| 2010/0173953 | A1 | 7/2010 | Grunenberg et al. |
| 2010/0173954 | A1 | 7/2010 | Wilhelm et al. |
| 2011/0015195 | A1 | 1/2011 | Dumas et al. |
| 2011/0195110 | A1 | 8/2011 | Smith et al. |
| 2012/0040925 | A1 | 2/2012 | Carter et al. |
| 2012/0040986 | A1 | 2/2012 | Riedl et al. |
| 2012/0142742 | A1 | 6/2012 | Riedl et al. |

FOREIGN PATENT DOCUMENTS

| WO | 03047523 A2 | 6/2003 |
| WO | 2005099661 A2 | 2/2005 |
| WO | WO 2005/009367 A2 | 2/2005 |
| WO | 2006125540 A1 | 11/2006 |
| WO | 2007/059154 A2 | 5/2007 |
| WO | 2007/059155 A1 | 5/2007 |

OTHER PUBLICATIONS

Yun Jung, Choi. "ImatiniB-Resistant Cell Lines are Sensitive to the RAF Inhibitor". American Society of Hematology, Dec. 10, 2002. vol. 100, No. 11.
Co-pending U.S. Appl. No. 09/776,936, filed Dec. 22, 1998.
Co-pending U.S. Appl. No. 13/401,272, filed Feb. 21, 2012.
U.S. Appl. No. 09/776,936; Claims and Office Action, Dec. 22, 1998.
U.S. Appl. No. 13/340,1272; Claims, Feb. 21, 2012.
U.S. Appl. No. 11/932,397; Claims and Office Action, Oct. 31, 2007.
U.S. Appl. No. 11/956,111; Claims and Office Action, Dec. 13, 2007.
U.S. Appl. No. 11/845,595; Claims and Office Action, Aug. 27, 2007.
U.S. Appl. No. 13/368,812; Claims, Feb. 8, 2012.
U.S. Appl. No. 13/208,010; Claims, Aug. 11, 2011.
U.S. Appl. No. 13/189,945; Claims, Jul. 25, 2011.
U.S. Appl. No. 10/848,567; Claims and Office Action, May 19, 2004.
U.S. Appl. No. 12/093,515; Claims and Office Action, May 13, 2008.
U.S. Appl. No. 11/754,082; Claims and Office Action, May 25, 2007.
U.S. Appl. No. 12/523,667; Claims and Office Action, Jul. 17, 2009.
U.S. Appl. No. 12/095,611; Claims, May 30, 2008.
U.S. Appl. No. 12/514,715; Claims and Office Action, May 13, 2009.
U.S. Appl. No. 12/444,974; Claims and Office Action, Apr. 9, 2009.
U.S. Appl. No. 12/514,129; Claims and Office Action, May 8, 2009.
U.S. Appl. No. 11/920,952; Claims and Office Action, Apr. 22, 2009.
U.S. Appl. No. 11/920,956; Claims and Office Action, Feb. 17, 2009.
U.S. Appl. No. 11/932,620; Claims and Office Action, Oct. 31, 2007.
U.S. Appl. No. 11/885,930; Claims and Office Action, Jun. 9, 2008.
U.S. Appl. No. 12/084,659; Claims and Office Action, Feb. 6, 2009.
U.S. Appl. No. 12/888,887; Claims and Office Action, Sep. 23, 2010.
Antonescu et al, "Acquired Resistance to Imatinib in Gastrointestinal Stromal Tumor occurs through Secondary Gene Mutation," Clinical Cancer Research, 2005, vol. 11, pp. 4182-4190, Jun. 1, 2005.
Tamborini et al. Gastroenterology, Jul. 2004, vol. 127, No. 1, pp. 294-299, (Abstract).
Adjei et al., "A Phase I study of BAY 43-9006 and gefitinib in patients with refractory or recurrent non-small-cell lung cancer (NSCLC)," Abstract #3067, Meeting: 2005 ASCO Annual Meeting, Category: Developmental Therapeutics: Molecular Therapeutics, Subcategory: Antiangiogenic or Antimetastatic agents. (2005).

(Continued)

Primary Examiner — Raymond Henley, III
(74) Attorney, Agent, or Firm — Millen, White, Zelano & Branigan, P.C.

(57) ABSTRACT

The present invention provides compositions and uses thereof for treating cancers which have acquired resistance to a KIT inhibitor by administering effective amounts of DAST (4{4-[3-(4-chloro-3-trifluoromethylphenyl)-ureido]-3-fluorophenoxy}-pyridine-2-carboxylic acid methylamide).

34 Claims, No Drawings

(56) References Cited

OTHER PUBLICATIONS

Tabellini et al., "Novel 2'-substituted, 3'-deoxy-phosphatidyl-myo-inositiol analogues reduce drug resistance in human leukaemia cell lines with an activated phosphoinositide 3-kinase/Akt pathway," British Journal Of Haematology, 126, 2004, pp. 574-582.

Norden-Zfoni, Anat, "Blood-Based Biomarkers of SU11248 Activity and Clinical Outcome in Patients with Metastatic Imatinib-Resistant Gastrointestinal Stromal Tumor," Clin. Cancer. Res. 2007; 13(9):2643-2650 May 1, 2007.

El-Deiry, Wafik S., "Meeting Report: The International Conference on Tumor Progression and Therapeutic Resistance", Cancer Research, 2005; vol. 65, No. 11, pp. 4475-4484.

Wilhelm et al., "BAY 43/9006 Exhibits Broad Spectrum Oral Antitumor Activity and Targets the RAF/MEK/ERK Pathway and Receptor Tyrosine Kinases Involved in Tumor Progression and Angiogenesis," Cancer Research, Oct. 1, 2004, vol. 64, pp. 7099-7109.

Al-Ali, H. et al., "High incidence of BCR-ABL kinase domain mutations and absence of mutations of the PDGFR and KIT activation loops in CML patients with secondary resistance to imatinib," The Hematology Journal, 2004, vol. 5, 55-60.

Carter, T.A. et al., "Inhibition of drug-resistant mutants of ABL, KIT, and EGF receptor kinases," PNAS, Aug. 2, 2005, vol. 102, No. 31, pp. 11011-17013.

Center for Drug Evaluation and Research, Approval Letter for Stivarga Tablets/ regorafenib submitted Sep. 27, 2012.

Center for Drug Evaluation and Research, Summary Review for Stivarga Tablets/ regoralenib submitted Apr. 27, 2012.

Meliado B. et al., "Molecular biology or renal cell carcinoma", Database accession No. EMB-2008397305; & Meliado B. et al.; "Molecular biology or renal cell carcinoma", Clinical and Translation Oncology 2006 IT LNKD-DOI: 10.1007/S12094-006-0116-7, vol. 8, Nol. 10, 2006, pp. 406-710, ISSN:1699-048X.

Nakano Yasuyuki et al., "Molecular evolution of acute myeloid leukemia in relapse: Unstable N-ras and FLT3 genes compared with p53 gene", British Journal of Haematology, vol. 104, No. 4, Mar. 1999 (199-03), pp. 659-664, ISSN: 0007-1048.

Al-All Haifa-Kathrin et al., "High incidence of BCR-ABL kinase domain mutations and absence of mutations of the PDGFR and KIT activation loops in CML patients with secondary resistance to Imatinib", Hematology Journal, McMillan, Basingstoke, GB, vol. 5, No. 1, Jan. 1, 2004, pp. 55-60, XP009136423, ISSN: 1466-4880.

Carter, Todd A., et al., "Inhibition of drug-resistant mutants of ABL, KIT, and EGF receptor kinases", Proceedings of the National Academy of Sciences, US, vol. 102, No. 31, Aug. 2, 2005, pp. 11011-11016, XP002440841, ISSN: 0027-8424, DOI: 10.1073/PNAS.0504952102.

Kwak et al., (PNAS (2005) 102(21), 7665-7670).

Faivre et al., J. of Clinical Oncology (2006): 24(1), 25-35.

Daub et al., Nature Reviews Drug Discovery 2004; 3: 1001-1010).

Demetri et al., (Journal of Clinical Oncology, 2004 ASCO Annual Meeting Proceedings (Post-Meeting Edition), 2004; vol. 22, No. 14S (Jul. 15 Supplement), #3001).

TREATMENT OF CANCERS WITH ACQUIRED RESISTANCE TO KIT INHIBITORS

RELATED APPLICATION DATA

This application is a 371 National Stage filing based on International Application PCT/US2008/051406, filed Jan. 18, 2008, which claims benefit of U.S. Provisional Application No. 60/885,728, filed Jan. 19, 2007.

SEQUENCE LISTING

The instant application contains a Sequence Listing which has been submitted via EFS-Web and is hereby incorporated by reference in its entirety. Said ASCII copy, created on May 25, 2010, is named BAYER143.txt, and is 689 bytes in size.

Cancer is a class of diseases characterized by two heritable properties: (1) uncontrolled cell division and (2) the ability of these cells to invade other tissues, either by direct growth into adjacent tissue (invasion) or by migration of cells to distant sites (metastasis). The hyper-proliferative properties initially give rise to a tumor or neoplasm. A tumor is considered a cancer when its cells acquire the ability to invade surrounding tissues, e.g., by breaking loose and entering the blood or lymph systems, or by forming secondary tumors at other sites in the body. The unregulated growth is caused by damaged DNA, resulting in mutations to vital genes that control cell division, the cell cycle, among other functions. One or more of these mutations, which can be inherited or acquired, can lead to uncontrolled cell division and cancer.

Cancers can be classified according to the tissue and cell type from which they arise. Cancers developing from epithelial cells are called carcinomas, and those from connective and muscle cells are called sarcomas. Additional cancers include those arising from hematopoietic cells (e.g., leukemia) and cancers of the nervous system.

In general, cancers appear to arise during a process in which an initial population of abnormal cells evolve into more aberrant cells through successive cycles of mutation and selection. More than 100 different genes have been identified which, when mutant, result in cancer. These so-called cancer-critical genes fall into two broad classes: oncogenes and tumor suppressor genes. Many cancer-critical genes play a role in the regulation of cell divisions, a highly complicated process involving multiple and parallel pathways. These include growth factors, cytokines, hormones, etc.

Cancer can cause many different symptoms, depending on the site and character of the malignancy and whether there is metastasis. A definitive diagnosis usually requires the microscopic examination of tissue obtained by biopsy. Once diagnosed, cancer is usually treated with surgery, chemotherapy and/or radiation.

If untreated, most cancers eventually cause death. Cancer is one of the leading causes of death in developed countries. It is estimated by the National Cancer Institute that approximately 9.8 million Americans were alive in January 2001 with a history of cancer. About 1,372,910 new cases of cancer were expected to be diagnosed in 2005, alone. In 2005, almost 600,000 Americans died of cancer, about 1 out of every 4 deaths. Many forms of cancer are associated with environmental factors, which may be avoidable. Smoking tobacco leads to more cancers than any other environmental factor.

Kinase inhibitors are being used successfully to treat cancers (e.g., Drevs et al., *Current Drug Targets,* 2003, 4, 113-121). However, some patients acquire a resistance to the drug's activity. In one embodiment, the present invention provides methods of treating a cancer in a subject in need thereof, comprising administering an effective amount of DAST to a subject having a cancer, wherein said cancer has acquired resistance to a KIT tyrosine kinase inhibitor. A tyrosine kinase inhibitor is a drug (i.e., a chemical compound) that blocks or reduces its kinase activity. Generally, a "tyrosine kinase activity" refers to the ability of the tyrosine kinase to auto-phosphorylate itself or trans-phosphorylate receptor subunits (or other substrates) by catalyzing the transfer of a phosphate from ATP (or another phosphate donor) to a tyrosine residue.

There are a number of well-documented instances where cancers have acquired resistance to a kinase inhibitor which previously had successfully been used to treat the cancer. The term "acquired resistance" indicates that the cancer becomes resistant and/or substantially less response to the effects of the drug after being exposed to it for a certain period of time. For example, gastrointestinal stromal tumors (GIST), a mesenchymal tumor of the intestinal tract, and chronic myelogenous leukemia (CML) are treated with imatinib (STI571 or Gleevac), a tyrosine kinase inhibitor that inhibits the kinase activity of BCR-ABL, ABL, KIT, and PDGFR. It has shown been shown that, while patients may benefit from the treatment initially, many patients subsequently develop resistance to the agent. In some cases, this acquired resistance has been shown to result from a secondary mutation in the gene associated with the cancer. For example, many GIST patients have an activating mutation in either the KIT or PDGFRA gene. A study of GIST patients with acquired resistance to imatinib showed secondary mutations in the KIT kinase domain. See, e.g., Antonescu et al, *Clin. Cancer Res.,* 11(11):41824190, 2005 and Heinrich et al., J. Clin. Oncology, 24(29), 4764-4774, 2006 A second site mutation in BCR-ABL is the predominant mechanism of imiatinib resistance in CML. See, e.g., Gorre et al., Science, 293:876-880, 2001. Acquired resistance has also been observed with other cancer drugs, including patients treated with EGFR-kinase inhibitors, such as gefitinib (Iressa) or erlotinib (Tarceva). See, e.g., Kobayshi et al., *N. Engl. J. Med.,* 352:786-792, 2005. Pao et al. (*PLoS Med.,* 2, e73, 2005) observed that patients with progressing lung tumors contained, in addition to a primary drug-sensitive mutation in EGFR, a secondary mutation in the kinase domain which led to drug-resistance.

Examples of KIT inhibitors to which drug resistance can be acquired includes, but is not limited to, e.g., imatinib mesylate, and derivatives and salts thereof; PP1 (4-Amino-5-(4-methylphenyl)-7-(t-butyl)pyrazolo[3,4-d]pyrimidine); MLN518 (CT53518); PD180970; SU112481 SU5416; SU5414; SU6597; SU6663; SU6561. See, also, Krystal et al., *Cancer Res.,* 2001, 61:3660-3668.

Resistance mutations often occur in the kinase catalytic domain interfering or weakening the interaction with its inhibitor. Resistance secondary mutations for KIT have been reported. These secondary mutations often occur in the "gate-keeper" residue, the amino acid residue that "guards" the ATP-binding pocket and which also can comprise the site which interacts with the inhibitor. See, e.g., Noble et al., *Science,* 303: 1800-1805, 2004.

While not being bound to any mechanism, examples of mutations in the KIT gene which are associated with resistance or acquired resistance include, but are not limited to, e.g., mutations in Exons 13, 14, and or 17; mutations at residues 654, 670, 716, 816, 820, 822, and 823, residues about 650-654, residues about 670-674, residues about 816-824, in the A-loop (activation), such as V654A (Exon 13), T670I (Exon 14), T670E, D716N, S709F (Exon 14), D816G, D816E (Exon 17), C809G, D816H, D816V, D820A, D820E, D820Y, D820G N822K, Y823D (Exon 17), and/or deletions and other amino acid substitutions at such positions, or adjacent positions. Generally, any cancer having a primary and/or secondary KIT gene mutation associated with resistance or acquired resistance to a KIT inhibitor can be treated with a compound in accordance with the present invention.

As shown in the examples, mutations can decrease the affinity of a kinase inhibitor, such as Imatinib (Gleevec), for the c-KIT protein, thereby decreasing the therapeutic efficacy of the drug. Table 1 shows specific examples where the binding affinity of Imatinib (Gleevec) decreased. Any disorder in which the affected tissue (e.g., cancer) becomes resistant or less responsive to a KIT inhibitor can be treated with DAST or derivatives thereof.

KIT (also known as c-kit, mast cell growth factor receptor, or stem cell growth factor receptor) is the human homology of the provirus of the Hardy-Zuckerman 4 feline sarcoma virus. KIT encodes a transmembrane tyrosine kinase receptor which is expressed in a number of tissues, and is required for normal hematopoiesis, melanogenesis, and gametogenesis. The gene itself, is mapped to 4q11-q12, includes 21 exons, and is alternatively spliced. See, e.g., Vandenbark et al., *Oncogene,* 7:1259-1266, 1992.

Over-expression and/or gain-of-function mutations in KIT can result in ligand-independent tyrosine kinase activity, autophosphorylation of KIT, uncontrolled cell proliferation, and stimulation of downstream signaling pathways. For example, KIT was overexpressed in both malignant and benign gastrointestinal stromal tumors (GIST) tumors. See, e.g., Koon et al., *Gut,* 2004, 53:235-240. KIT is also expressed in acute myeloid leukemia, mast cell tumors, SCLC, germ cell tumors, breast cancer, and neuroblastoma.

Activating mutations in the KIT gene are associated with many types of GIST, the most common mesenchymal neoplasm in the human digestive tract. For example, Hirota et al., *Science,* 279:577-580, 1998, showed that of 49 mesenchymal tumors, 94% of them expressed an activated KIT. GISTs include a spectrum of tumors, including both benign and malignant types, and which occur at all levels of the gastrointestinal tract (e.g., stomach, small intestine, large intestine, rectum, etc.)

Cancers which are initially sensitive to a KIT inhibitor, but which have acquired resistance to it, can be treated in accordance with the present invention. Cancers having mutations in Exon 11 (from amino acid positions 550-582; see, e.g., Table 2) of the KIT gene are of particular relevance, and more preferably within codons 550-560. This region can also be referred to as the juxtamembrane domain. Specific examples include, but are not limited to: 1) deletion of amino acid residues 557-558; 2) deletion of amino acid residues 551-555; 3) deletion of amino acid residues 550-558; 4) deletion of amino acid residues 559-560; 5) deletion of amino acid residues 557-561; 6) deletion of amino acid residues 554-558; 7) deletion of amino acid residues 552-557; 8) mutations at residue 559, including V559D, V559A, or V559G; 9) mutations at residue 560, including V560D, V560E, or V560G; 10) W557S, alone, or in combination with a deletion of amino acids 552-556; 11) mutations at amino acid residue 557, including W557R; 12) mutations at amino acid residue 576, including L576P; 13) InsQL576-577. These mutations can be alone, or combined with other mutations, including with any of the specifically mentioned mutations. See, also, Lasota et al., *Am. J. Path.,* 154:53-60, 1999.

Drug resistant cancers associated with other KIT mutations can be treated as well, especially those which are sensitive to KIT inhibitors. These include, e.g., systemic mastocytosis, e.g., having a F522C mutation (Akin et al., *Blood,* 2004, 193:3222-3225) and K509I (Zhang et al., 2005, Leuk. Res., September 21); testicular seminomas, e.g., having imatinib mesylate sensitive mutations at amino acid residues 822 and 823, such as N822K and Y823D (e.g., Kemmer et al., *Am. J. Pathol.,* 2004, 164:305-313, 2004).

Analysis of the gene mutations associated with cancer (e.g., GIST) having KIT mutation can be routinely determined. For example, PCR can be utilized to amplify specific regions using the published sequences of the human KIT gene. See, e.g., Andre et al., *Genomics,* 1997, 39:216-226. For amplification of Exon 11, see, e.g., Lasota et al., *Am. J. Path.,* 154:53-60, 1999.

Diarylureas are a class of serine-threonine kinase inhibitors as well as tyrosine kinase inhibitors known in the art. The following publications illustrate their utility as active ingredients in pharmaceutical compositions for the treatment of hyper-proliferative diseases, such as cancer:

Smith al., *Bioorg. Med. Chem. Lett.* 2001, 11, 2775-2778,
Lowinger et al., *Clin. Cancer Res.* 2000, 6(suppl.), 335
Lyons et al., *Endocr.-Relat. Cancer* 2001, 8, 219-225.
Riedl et al., *Book of Abstracts,* $92^{nd}$ AACR Meeting, New Orleans, La., USA, abstract 4956.
Khire et al., *Book of Abstracts,* $93^{rd}$ AACR Meeting, San Francisco, Calif., USA, abstract 4211.
Lowinger et al., *Curr. Pharm. Design* 2002, 8, 99-110.
Carter et al., *Book of Abstracts,* $92^{hd}$ AACR Meeting, New Orleans, La., USA, abstract 4954.
Vincent et al., *Book of Abstracts,* $38^{th}$ ASCO Meeting, Orlando, Fla., USA, abstract 1900.
Hilger et al., *Book of Abstracts,* $38^{th}$ ASCO Meeting, Orlando, Fla., USA, abstract 1916.
Moore et al., *Book of Abstracts,* $38^{th}$ ASCO Meeting, Orlando, Fla., USA, abstract 1816.
Strumberg et al., *Book of Abstracts,* $38^{th}$ ASCO Meeting, Orlando, Fla., USA, abstract 121.

Omega-Carboxyaryl diphenyl ureas are disclosed in WO00/42012 (published Jul. 20, 2000) and WO00/41698 (published Jul. 20, 2000). DAST, the diphenyl urea referred to as 4{4-[3-(4-chloro-3-trifluoromethylphenyl)-ureido]-3-fluorophenoxy}-pyridine-2-carboxylic acid methyl amide herein, is disclosed in WO05/009961 (published Feb. 3, 2005) and is described as a potent inhibitor of raf, VEGFR-2, p38, and PDGFR kinases. These enzymes are all molecular targets of interest for the treatment of hyper-proliferative diseases, including cancer. Solid dispersions of DAST are described in WO06/026500 (published Mar. 9, 2006).

Nonetheless, the present invention relates to using DAST to treat a cancer, such as those mentioned above, which have acquired resistance to a KIT inhibitor, irrespective of the molecular mechanism responsible for it.

The present invention provides methods of treating cancers comprising, e.g., comprising administering to a subject in need thereof an effective amount of DAST, wherein the cancer is treated.

Examples of cancers that can be treated with imatinib, include, but not limited to: Accelerated Phase Chronic Myelogenous Leukemia; Acute Erythroid Leukemia; Acute Lymphoblastic Leukemia; Acute Lymphoblastic Leukemia in Remission; Acute Lymphocytic Leukemia; Acute Monoblastic and Acute; Monocytic Leukemia; Acute Myelogenous Leukemia; Acute Myeloid Leukemia; Adenocarcinoma of the Prostate; Adenoid Cystic Carcinoma of the Head and Neck; Advanced Gastrointestinal Stromal Tumor; Agnogenic Myeloid; Metaplasia; Anaplastic Oligodendroglioma; Astrocytoma; B-Cell Adult Acute Lymphoblastic Leukemia; Blastic Phase Chronic Myelogenous Leukemia; Bone Metastases; Brain Tumor; Breast Cancer; Cancer; Central Nervous System Cancer; Childhood Acute Lymphoblastic Leukemia; Childhood Acute Lymphoblastic Leukemia in Remission; Childhood Central Nervous System Germ Cell Tumor; Childhood Chronic Myelogenous Leukemia; Childhood Soft Tissue Sarcoma; Chordoma; Chronic Eosinophilic Leukemia (CEL); Chronic Idiopathic Myelofibrosis; Chronic Myelogenous Leukemia; Chronic Myeloid Leukemia; Chronic Myelomonocytic Leukemia; Chronic Phase Chronic Myelogenous Leukemia; Colon Cancer; Colorectal Cancer; Dermatofibrosarcoma; Dermatofibrosarcoma Protuberans (DFSP); Desmoid Tumor; Eosinophilia; Epidemic Kaposi's Sarcoma; Essential Thrombocythemia; Ewing's Family of Tumors; Extensive Stage Small Cell Lung Cancer; Fallopian Tube Cancer; Familiar Hypereosinophilia; Fibrosarcoma; Gastric Adenocarcinoma; Gastrointestinal Neoplasm; Gastrointestinal Stromal Tumor; Glioblastoma; Glioma; Gliosarcoma; Grade I Meningioma; Grade II Meningioma; Grade III Meningioma; Hematopoietic and Lymphoid Cancer; High-Grade Childhood Cerebral Astrocytoma; Hypereosinophilic Syndrome; Idiopathic Pulmonary Fibrosis; L1 Adult Acute Lymphoblastic Leukemia; L2 Adult Acute Lymphoblastic Leukemia; Leukemia, Lymphocytic, Acute L2; Leukemia, Myeloid, Chronic; Leukemia, Myeloid, Chronic Phase; Liver Dysfunction and Neoplasm; Lung Disease; Lymphoid Blastic Phase of Chronic Myeloid Leukemia; Male Breast Cancer; Malignant Fibrous Histiocytoma; Mastocytosis; Meningeal Hemangiopericytoma; Meningioma; Meningioma; Meningioma; Metastatic Cancer; Metastatic Solid Tumors; Myelofibrosis; Myeloid Leukemia, Chronic; Myeloid Leukemia, Chronic Accelerated-Phase; Myeloid Leukemia, Chronic, Chronic-Phase; Myeloid Metaplasia; Myeloproliferative Disorder (MPD) with Eosinophilia; Neuroblastoma; Non-T, Non-B Childhood Acute Lymphoblastic Leukemia; Oligodendroglioma; Osteosarcoma; Ovarian Germ Cell Tumor; Ovarian Low Malignant Potential Tumor; Ovarian Neoplasms; Pancreatic Cancer; Pelvic Neoplasms; Peritoneal Cavity Cancer; Peritoneal Neoplasms; Philadelphia Chromosome Positive Chronic Myelogenous Leukemia; Philadelphia Positive Acute Lymphoblastic Leukemia; Philadelphia Positive Chronic Myeloid Leukemia in Myeloid Blast Crisis; Polycythemia Vera; Pulmonary Fibrosis; Recurrent Adult Brain Tumor; Recurrent Adult Soft Tissue Sarcoma; Recurrent Breast Cancer; Recurrent Colon Cancer; Recurrent Esophageal Cancer; Recurrent Gastric Cancer; Recurrent Glioblastoma Multiforme (GBM); Recurrent Kaposi's Sarcoma; Recurrent Melanoma; Recurrent Merkel Cell Carcinoma; Recurrent Ovarian Epithelial Cancer; Recurrent Pancreatic Cancer; Recurrent Prostate Cancer; Recurrent Rectal Cancer; Recurrent Salivary Gland Cancer; Recurrent Small Cell Lung Cancer; Recurrent Tumors of the Ewing's Family; Recurrent Uterine Sarcoma; Relapsing Chronic Myelogenous Leukemia; Rheumatoid Arthritis; Salivary Gland Adenoid Cystic Carcinoma; Sarcoma; Small Cell Lung Cancer; Stage II Melanoma; Stage II Merkel Cell Carcinoma; Stage III Adult Soft Tissue Sarcoma; Stage III Esophageal Cancer; Stage III Merkel Cell Carcinoma; Stage III Ovarian Epithelial Cancer; Stage III Pancreatic Cancer; Stage III Salivary Gland Cancer; Stage IIIB Breast Cancer; Stage IIIC Breast Cancer; Stage IV Adult Soft Tissue Sarcoma; Stage IV Breast Cancer; Stage IV Colon Cancer; Stage IV Esophageal Cancer; Stage IV Gastric Cancer; Stage IV Melanoma; Stage IV Ovarian Epithelial Cancer; Stage IV Prostate Cancer; Stage IV Rectal Cancer; Stage IV Salivary Gland Cancer; Stage IVA Pancreatic Cancer; Stage IVB Pancreatic Cancer; Systemic Mastocytosis; T-Cell Childhood Acute Lymphoblastic Leukemia; Testicular Cancer; Thyroid Cancer; Unresectable or Metastatic Malignant Gastrointestinal Stromal Tumor (GIST); Unspecified Adult Solid Tumor; Untreated Childhood Brain Stem Glioma; Uterine Carcinosarcoma, and Uterine Sarcoma.

The phrase "effective amount" indicates the amount of DAST which is effective to treat any symptom or aspect of the cancer. Effective amounts can be determined routinely. Further guidance on dosages and administration regimens is provided below.

The term "treating" is used conventionally, e.g., the management or care of a subject for the purpose of combating, alleviating, reducing, relieving, improving, etc., one or more of the symptoms associated with a cancer, including all cancers mentioned herein. Administering effective amounts of DAST can treat one or more aspects of the cancer disease, including, but not limited to, causing tumor regression; causing cell death; causing apoptosis; causing necrosis; inhibiting cell proliferation; inhibiting tumor growth; inhibiting tumor metastasis; inhibiting tumor migration; inhibiting tumor invasion; reducing disease progression; stabilizing the disease; reducing or inhibiting angiogenesis; prolonging patient survival; enhancing patient's quality of life; reducing adverse symptoms associated with cancer; and reducing the frequency, severity, intensity, and/or duration of any of the aforementioned aspects.

Any cancer can be treated in accordance of the present invention, irrespective of the type or cause of the cancer, and irrespective of the genetic lesions associated with. Examples of cancers which can be treated include, but are not limited to, GIST, acute myeloid leukemia, mast cell tumors, SCLC, germ cell tumors, breast cancer, neuroblastoma, sinonasal lymphoma, etc.

Cancers which can be treated include, e.g., cancers which are primary; which arise from a primary tumor at a secondary metastatic site; which have been treated by surgery (e.g., entirely removed, surgical resection, etc); which have been treated by chemotherapy, radiation, radio frequency ablation, and/or any other adjunct to drug therapy. Any subject can be in accordance with the present invention, including, e.g., mammals, such as mice, rats, dogs, cats, non-human primates, monkeys, and humans.

The ability of DAST to treat a cancer with acquired resistance to a KIT inhibitor can be routinely determined. For example, the IL-3-dependent murine hematopoietic cell line, Ba/F3, can be cultured independently of IL-3 when transfected with constitutively active KIT (e.g., having a deletion of amino acid residues 557-558). See, e.g., Tsujimura et al., *Blood,* 1999, 93:1319-1329. In the presence of a KIT inhibitor, such as imatinib, cells expressing the constitutively active KIT polypeptide undergo cell death as a result of KIT inhibition. The presence of a second mutation that confers resistance to the KIT inhibitor rescues the cells. Cells expressing the double-mutation (activating; KIT resistance) are cultured in the presence of DAST. Those cells which die are sensitive to DAST, indicating its usefulness in treating patients who have acquired resistance to the KIT inhibitor.

Specific examples of cancers which can be treated in accordance with the present invention include cancers have a deletion of residues 557-558, and which have at least one of the following mutations: V654A, T670I, D820Y, N822K, and Y823D.

The present invention also provides methods of determining whether to treat a subject having cancer with DAST, comprising determining the presence of a mutation in a KIT gene, wherein said mutation is an activating and/or KIT-inhibitor resistance mutation, and administering DAST to a subject having one or more pre-determined mutations. Activating and KIT-inhibitor resistance mutations have been described above. A subject who is resistant to a KIT inhibitor can be screened for the presence of an activating and/or resistance mutation (such as those listed above), a subject having the mutation(s) can be treated with DAST.

The term "DAST" as used herein refers to the compound: 4{4-[3-(4-chloro-3-trifluoromethylphenyl)-ureido]-3-fluorophenoxy}-pyridine-2-carboxylic acid methylamide of the formula I below including all polymorphs, hydrates, solvates, pharmaceutically acceptable salts or combinations thereof. Also included are the metabolites of 4{4-[3-(4-chloro-3-trifluoromethylphenyl)-ureido]-3-fluorophenoxy}-pyridine-2-carboxylic acid methylamide and prodrugs of 4{4-[3-(4-chloro-3-trifluoromethylphenyl)-ureido]-3-fluorophenoxy}-pyridine-2-carboxylic acid methylamide prepared by conventional techniques.

Suitable pharmaceutically acceptable salts are well known to those skilled in the art and include salts of inorganic and organic acids, such as hydrochloric acid, hydrobromic acid, sulfuric acid, phosphoric acid, methanesulphonic acid, trifluoromethanesulfonic acid, benzenesulfonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include salts of inorganic bases, such as salts containing alkaline cations (e.g., $Li^+$ $Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU).

Solvates for the purposes of the invention are those forms of the compound where solvent molecules form a complex in the solid state and include, but are not limited to for example ethanol and methanol. Hydrates are a specific form of solvates, where the solvent molecule is water.

The metabolites of DAST include oxidized derivatives wherein one or more of the urea nitrogens shown in of Formula I are substituted with a hydroxyl group. The metabolites of DAST also include analogs where the methylamide group shown in Formula I is hydroxylated then de-methylated by metabolic degradation. The metabolites of DAST further include oxidized derivatives where the pyridine nitrogen atom shown in of Formula I is in the N-oxide form (e.g. carries a hydroxy substituent) leading to those structures referred to in the art as 1-oxo-pyridine and 1-hydroxy-pyridine.

DAST can be further modified with labile functional groups that are cleaved after in vivo administration to furnish the parent active agent and the pharmacologically inactive derivatizing (functional) group. These derivatives, commonly referred to as prodrugs, can be used, for example, to alter the physicochemical properties of the active agent, to target the active agent to a specific tissue, to reduce undesirable side effects and/or to alter the pharmacokinetic and pharmacodynamic properties of the active agent (e.g., solubility, absorption, biostability and release time. see "Pharmaceutical Dosage Form and Drug Delivery Systems" (Sixth Edition), edited by Ansel et al., published by Williams & Wilkins, pages 27-29, (1995) which is hereby incorporated by reference), Suitable including N-dealkylation, O-dealkylation, aliphatic hydroxylation, aromatic hydroxylation, N-oxidation, S-oxidation, deamination, hydrolysis reactions, glucuronidation, sulfation and acetylation (see Goodman and Gilman's The Pharmacological Basis of Therapeutics (Ninth Edition), editor Molinoff et al., pub. by McGraw-Hill, pages 11-13, (1996), which is hereby incorporated by reference).

Suitable prodrugs of DAST include, e.g., well-tolerated, pharmaceutically acceptable esters such as alkyl esters including methyl, ethyl, propyl, isopropyl, butyl, isobutyl or pentyl esters. Additional esters such as phenyl-$C_1$-$C_5$ alkyl esters may be used, although methyl ester is preferred.

Methods for synthesizing prodrugs are described in the following reviews on the subject, which are incorporated herein by reference for their description of these methods:

Higuchi, T.; Stella, V. eds. *Prodrugs as Novel Drug Delivery Systems*. ACS Symposium Series. American Chemical Society: Washington, D.C. (1975).

Roche, E. B. *Design of Biopharmaceutical Properties through Prodrugs and Analogs*. American Pharmaceutical Association: Washington, D.C. (1977).

Sinkula, A. A.; Yalkowsky, S. H. *J Pharm Sci.* 1975, 64, 181-210.

Stella, V. J.; Charman, W. N. Naringrekar, V. H. *Drugs* 1985, 29, 455-473.

Bundgaard, H., ed. *Design of Prodrugs*. Elsevier: New York (1985).

Stella, V. J.; Himmelstein, K. J. *J. Med. Chem.* 1980, 23, 1275-1282.

Han, H-K; Amidon, G. L. *AAPS Pharmsci* 2000, 2, 1-11.

Denny, W. A. *Eur. J. Med. Chem.* 2001, 36, 577-595.

Wermuth, C. G. in Wermuth, C. G. ed. *The Practice of Medicinal Chemistry* Academic Press: San Diego (1996), 697-715.

Balant, L. P.; Doelker, E. in Wolff, M. E. ed. *Burgers Medicinal Chemistry And Drug Discovery* John Wiley & Sons: New York (1997), 949-982.

Formula I is as follows:

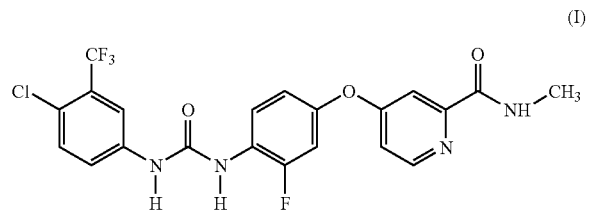 [SMILES: CNC(=O)c1cc(Oc2ccc(NC(=O)Nc3ccc(Cl)c(C(F)(F)F)c3)c(F)c2)ccn1]

(I)

Examples of the preparation of DAST, salts thereof and pharmaceutical compositions thereof follow.

Preparation of the Intermediate:
4-amino-3-fluorophenol

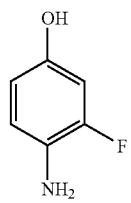

To a dry flask purged with Argon was added 10% Pd/C (80 mg) followed by 3-fluoro-4-nitrophenol (1.2 g, 7.64 mmol) as a solution in ethyl acetate (40 mL). The mixture was stirred under an H₂ atmosphere for 4 h. The mixture was filtered through a pad of Celite and the solvent was evaporated under reduced pressure to afford the desired product as a tan solid (940 mg, 7.39 mmol; 97% yield); $^1$H-NMR (DMSO-$d_6$) 4.38 (s, 2H), 6.29-6.35 (m, 1H), 6.41 (dd, J=2.5, 12.7, 1H), 6.52-6.62 (m, 1H), 8.76 (s, 1H).

Preparation of the Starting Material 1: 4-(4-amino-3-fluorophenoxy)pyridine-2-carboxylic acid methylamide

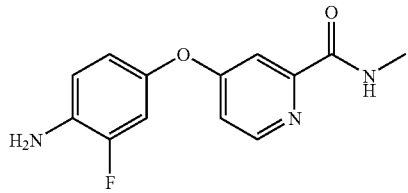 [SMILES: CNC(=O)c1cc(Oc2ccc(N)c(F)c2)ccn1]

A solution of intermediate 4-amino-3-fluorophenol, (500 mg, 3.9 mmol) in N,N-dimethylacetamide (6 mL) cooled to 0° C. was treated with potassium tert-butoxide (441 mg, 3.9 mmol), and the brown solution was allowed to stir at 0° C. for 25 min. To the mixture was added 4-chloro-N-methyl-2-pyridinecarboxamide, (516 mg, 3.0 mmol) as a solution in dimethylacetamide (4 mL). The reaction was heated at 100° C. for 16 h. The mixture was cooled to room temperature, quenched with H₂O (20 mL), and extracted with ethylacetate (4×40 mL). The combined organics were washed with H₂O (2×30 mL), dried (MgSO₄), and evaporated to afford a red-brown oil. $^1$H-NMR indicated the presence of residual dimethylacetamide, thus the oil was taken up in diethylether (50 mL) and was further washed with brine (5×30 mL). The organic layer was dried (MgSO₄) and concentrated to give 950 mg of the desired product, starting material 1, as a red-brown solid, which was used in the next step without purification.

EXAMPLE 1

Preparation of DAST: 4{4-[3-(4-chloro-3-trifluoromethylphenyl)-ureido]-3-fluorophenoxy}-pyridine-2-carboxylic acid methylamide

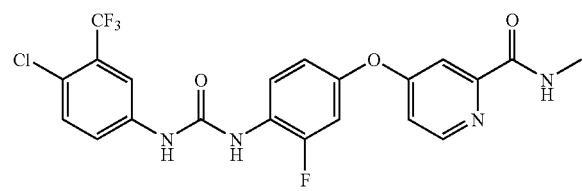 [SMILES: CNC(=O)c1cc(Oc2ccc(NC(=O)Nc3ccc(Cl)c(C(F)(F)F)c3)c(F)c2)ccn1]

To a solution of 4-(4-amino-3-fluorophenoxy)pyridine-2-carboxylic acid methylamide (starting material 1, 177 mg, 0.68 mmol) in toluene (3 mL) was added 4-chloro-3-(trifluoromethyl)phenyl isocyanate (150 mg, 0.68 mmol). The mixture was stirred at room temperature for 72 h. The reaction was concentrated under reduced pressure and the residue was triturated with diethylether. The resulting solid was collected by filtration and dried in vacuo for 4 h to afford the title compound (155 mg, 0.32 mmol; 47% yield); $^1$H-NMR (DMSO-$d_6$) 2.78 (d, J=4.9, 3H), 7.03-7.08 (m, 1H), 7.16 (dd, J=2.6, 5.6, 1H), 7.32 (dd, J=2.7, 11.6, 1H), 7.39 (d, J=2.5, 1H), 7.60 (s, 2H), 8.07-8.18 (m, 2H), 8.50 (d, J=5.7, 1H), 8.72 (s, 1H), 8.74-8.80 (m, 1H), 9.50 (s, 1H); MS (HPLC/ES) 483.06 m/z=(M+1).

EXAMPLE 2

Preparation of the Salt: 4{4-[3-(4-chloro-3-trifluoromethylphenyl)-ureido]-3-fluorophenoxy}-pyridine-2-carboxylic acid methylamide hydrochloride The compound of Example 1 as a free base (2.0 g) was dissolved in anhydrous tetrahydrofuran (15 mL) and a 4M HCl/dioxane was added (excess). The solution was then concentrated in vacuo to afford 2.32 grams of off-white solids. The crude salt was dissolved in hot ethanol (125 mL), activated carbon was added and the mixture heated at reflux for 15 minutes. The hot suspension was filtered through a pad of Celite 521 and allowed to cool to room temperature. The flask was placed in a freezer overnight. The crystalline solids were collected by suction filtration, washed with ethanol, then hexane and air-dried. The mother liquors were concentrated down and crystallization (in freezer) allowed taking place overnight. A second crop of solids was collected and combined with the first crop. The colorless salt was dried in a vacuum oven at 60° C. over two days. Yield of hydrochloride salt obtained 1.72 g (79%).

Melting point: 215° C.
Elemental analysis:

|    | Calcd. | Found |
|----|--------|-------|
| C  | 48.57  | 48.68 |
| H  | 3.11   | 2.76  |
| N  | 10.79  | 10.60 |
| Cl | 13.65  | 13.63 |
| F  | 14.63  | 14.88 |

EXAMPLE 3

Preparation of the Salt: 4{4-[3-(4-chloro-3-trifluoromethylphenyl)-ureido]-3-fluorophenoxy}-pyridine-2-carboxylic acid methylamide mesylate The compound of Example 1 as a free base (2.25 g) was dissolved in ethanol (100 mL) and a stock solution of methanesulfonic acid (excess) was added. The solution was then concentrated in vacuo to afford a yellow oil. Ethanol was added and concentration repeated, affording 2.41 g of off-white solids. The crude salt was dissolved in hot ethanol (~125 mL) and then cooled slowly to crystallize. After reaching room temperature, the flask was placed in a freezer overnight. The colorless crystalline material was collected by suction filtration; the filter cake was washed with ethanol, then hexane and air-dried, to afford 2.05 g of material, which was dried in a vacuum oven at 60° C. overnight.

Melting point: 231° C.
Elemental analysis:

|   | Calcd. | Found |
|---|--------|-------|
| C | 45.64  | 45.34 |
| H | 3.31   | 3.08  |
| N | 9.68   | 9.44  |

-continued

|    | Calcd. | Found |
|----|--------|-------|
| Cl | 6.12   | 6.08  |
| F  | 13.13  | 13.42 |
| S  | 5.54   | 5.59  |

EXAMPLE 4

Preparation of the Salt: 4{4-[3-(4-chloro-3-trifluoromethylphenyl)-ureido]-3-fluorophenoxy}-Pyridine-2-carboxylic acid methylamide phenylsulfonate The compound of Example 1 as a free base (2.25 g) was suspended in ethanol (50 mL) and benzensulfonic acid (0.737 g) in ethanol (50 mL) was added. The mixture was heated with vigorous stirring. All solid material dissolved to give a reddish solution. The solution was allowed to cool to room temperature and the flask scratched. Crystal formation was slow, some seeds were found, added to solution and placed in freezer overnight. Grayish-tan solids had formed in the flask; the material was broken up & collected by suction filtration. The solids were washed with ethanol, then hexane and air-dried. Weighed product: 2.05 g, 69% yield.
Melting point: 213° C.
Elemental Analysis:

|    | Calcd. | Found |
|----|--------|-------|
| C  | 50.59  | 50.24 |
| H  | 3.30   | 3.50  |
| N  | 8.74   | 8.54  |
| F  | 11.86  | 11.79 |
| Cl | 5.53   | 5.63  |
| S  | 5.00   | 5.16  |

EXAMPLE 5

Preparation of a 1+4 solid dispersion of 4{4-[3-(4-chloro-3-trifluoromethylphenyl)-ureido]-3-fluorophenoxy}-Pyridine-2-carboxylic acid methyl amide with polyvinylpyrrolidone In an uncapped vial, one part of the compound of Example 1 as a free base was mixed with four parts polyvinylpyrrolidone (PVP-25/Kollidon® 25), and dissolved in a sufficient amount of a 1:1 mixture of acetone and ethanol, until all powders are in solution. The uncapped vial was placed into a vacuum oven set at 40° C., and let dry for at least 24-48 hours.

EXAMPLE 6

Preparation of a 1+3 Solid Dispersion of 4{4-[3-(4-chloro-3-trifluoromethylphenyl)-ureido]-3-fluorophenoxy}-pyridine-2-carboxylic acid methyl amide with polyvinylpyrrolidone One part of the compound of Formula I as base and three parts of polyvinylpyrrolidone (PVP 25/Kollidon® 25) were dissolved in 30 parts of a 80:20 acetone/ethanol mixture (w/w). Using a rotary vacuum evaporator the solvent was removed at 70° C. The dry residue was removed from the evaporation flask and sieved (630 μm).

EXAMPLE 7

Preparation of a 1+7 Solid Dispersion of 4{4-[3-(4-chloro-3-trifluoromethylphenyl)-ureido]-3-fluorophenoxy}-Pyridine-2-carboxylic acid methyl amide with polyvinylpyrrolidone One part of the compound of Formula I as base and seven parts PVP 25 were dissolved in 30 parts of a 80:20 acetone/ethanol mixture (w/w). Using a rotary vacuum evaporator the solvent was removed at 70° C. The dry residue was removed from the evaporation flask and sieved (630 μm).

EXAMPLE 8

Solid Dispersion of 4{4-[3-(4-chloro-3-trifluoromethylphenyl)-ureido]-3-fluorophenoxy}-pyridine-2-carboxylic acid methyl amide with hydroxypropyl cellulose (HPC) prepared by melt extrusion Two parts of the compound of Formula I as base were mixed with one part of Maltitol and seven parts of HPC-M. The mixture was extruded using a lab twin screw extruder at a temperature of 160-200° C. The extruded material was cut and subsequently milled using an impact lab mill. The resulting powder can be used as it is or it can be further formulated for example to sachet, capsule or tablet formulations.

EXAMPLE 9

Solid Dispersion of 4{4-[3-(4-chloro-3-trifluoromethylphenyl)-ureido]-3-fluorophenoxy}-Pyridine-2-carboxylic acid methyl amide with PVP and croscarmellose sodium A solution of 0.4 kg of the of the compound of Formula I as base and 1.2 kg of PVP 25 in a mixture of 6.4 kg acetone and 1.6 kg ethanol was prepared. Using a fluidized bed vacuum granulator this solution was sprayed onto a powder bed of 1.6 kg croscarmellose sodium at a temperature of 60-70° C. After drying the product was sieved (1 mm). The granulate can be used as it is or it can be further formulated for example to sachet, capsule or tablet formulations.

EXAMPLE 10

Solid Dispersion of 4{4-[3-(4-chloro-3-trifluoromethylphenyl)-ureido]-3-fluorophenoxy}-Pyridine-2-carboxylic acid methyl amide with PVP and sodium starch glycolate This material was prepared in a similar way as described in Example 9, except that the solution is sprayed onto a powder bed of 1.6 kg sodium starch gycolate Type A (Explotab®)

EXAMPLE 11

Solid Dispersion of 4{4-[3-(4-chloro-3-trifluoromethylphenyl)-ureido]-3-fluorophenoxy}-Pyridine-2-carboxylic acid methyl amide with PVP and croscarmellose sodium A solution of 0.4 kg of the of the compound of Formula I as base and 1.6 kg of PVP 25 in a mixture of 6.4 kg acetone and 1.6 kg ethanol was prepared. Using a fluidized bed vacuum granulator this solution was sprayed onto a powder bed of 2 kg croscarmellose sodium at a temperature of 60-70° C. After

EXAMPLE 12

Solid Dispersion of 4{4-[3-(4-chloro-3-trifluoromethylphenyl)-ureido]-3-fluorophenoxy}-pyridine-2-carboxylic acid methyl amide with PVP, croscarmellose sodium and microcrystalline cellulose This material was prepared in a similar way as described in Example 11, except that the solution was sprayed onto a powder bed consisting of 1 kg croscarmellose sodium and 1 kg microcrystalline cellulose.

EXAMPLE 13

Solid Dispersion of 4{4-[3-(4-chloro-3-trifluoromethylphenyl)-ureido]-3-fluorophenoxy}-pyridine-2-carboxylic acid methyl amide with HPC-SL and croscarmellose sodium A solution of 0.4 kg of the of the compound of Formula I as base and 1.6 kg of HPC-SL in 20 kg acetone was prepared. Using a fluidized bed vacuum granulator this solution was sprayed onto a powder bed of 2 kg croscarmellose sodium at a temperature of 40-60° C. After drying the product was sieved (1 mm). The granulate can be used as it is or it can be further formulated for example to sachet, capsule or tablet formulations.

EXAMPLE 14

Solid Dispersion of 4{4-[3-(4-chloro-3-trifluoromethylphenyl)-ureido]-3-fluorophenoxy}-pyridine-2-carboxylic acid methyl amide with HPC-L and croscarmellose sodium A solution of 0.4 kg of the of the compound of Formula I as base and 1.6 kg of HPC-L in 28 kg acetone was prepared. Using a fluidized bed vacuum granulator this solution was sprayed onto a powder bed of 2 kg croscarmellose sodium at a temperature of 40-60° C. After drying the product was sieved (1 mm). The granulate can be used as it is or it can be further formulated for example to sachet, capsule or tablet formulations.

EXAMPLE 15

Tablets Containing a Solid Dispersion of 4{4-[3-(4-chloro-3-trifluoromethylphenyl)-ureido]-3-fluorophenoxy}-Pyridine-2-carboxylic acid methyl amide The granulate of Example 11 was roller compacted and screened 3 and 1 mm. Subsequently the compacted granulate was blended with 0.54 kg croscarmellose sodium, 24 g colloidal anhydrous silica and 36 g magnesium stearate. This ready-to-press blend was compressed on a rotary tablet press to tablets containing 20, 50 an 100 mg of the compound of Formula I. The tablets may be film-coated for light protection.

EXAMPLE 16

Tablets Containing a Solid Dispersion of 4{4-[3-(4-chloro-3-trifluoromethylphenyl)-ureido]-3-fluorophenoxy}-pyridine-2-carboxylic acid methyl amide The granulate of Example 12 was roller compacted and screened 3 and 1 mm. Subsequently the compacted granulate was blended with 0.54 kg croscarmellose sodium, 24 g colloidal anhydrous silica and 36 g magnesium stearate. This ready-to-press blend was compressed on a rotary tablet press to tablets containing 20, 50 an 100 mg of the compound of Formula I. The tablets may be film-coated for light protection.

EXAMPLE 17

Tablets Containing a Solid Dispersion of 4{4-[3-(4-chloro-3-trifluoromethylphenyl)-ureido]-3-fluorophenoxy}-Pyridine-2-carboxylic acid methyl amide A solution of 0.4 kg of the of the compound of Formula I as base and 1.2 kg of PVP 25 in a mixture of 6.4 kg acetone and 1.6 kg ethanol was prepared. Using a fluidized bed vacuum granulator this solution was sprayed onto a powder bed consisting of 0.8 kg croscarmellose sodium and 0.8 kg microcrystalline cellulose at a temperature of 60-70° C. After drying the product is sieved (1 mm). The granulate is roller compacted and screened 3 and 1 mm. Subsequently the compacted granulate was blended with 1.34 kg croscarmellose sodium, 24 g colloidal anhydrous silica and 36 g magnesium stearate. This ready-to-press blend is compressed on a rotary tablet press to tablets containing 20, 50 an 100 mg of the compound of Formula I. The tablets may be film-coated for light protection.

The specific dose level and frequency of dosage may vary, depending upon a variety of factors, including the activity of the active agent, its metabolic stability and length of action, rate of excretion, mode and time of administration, the age, body weight, health condition, gender, diet, baseline hematologic and biologic parameters (e.g., WBCs, granulocytes, platelets, hemoglobin, creatinine, bilirubin, albumin, etc.), etc., of the subject, and the severity, intensity, stage of the cancer, primary site of cancer, size of cancer lesion, presence or extent of metastases, surgical status, disease progression (i.e., aggressive), etc. of the disease.

DAST can be administered in any form by any effective route, including, e.g., oral, parenteral, enteral, intraperitoneal, topical, transdermal (e.g., using any standard patch), ophthalmic, nasally, local, non-oral, such as aerosol, spray, inhalation, subcutaneous, intravenous, intramuscular, buccal, sublingual, rectal, vaginal, intra-arterial, intrathecal, intratumoral, etc. DAST can be administered directly to the site of a tumor, either pre- or post-operatively. It can be administered alone, or in combination with any ingredient(s), active or inactive.

DAST can be administered by the oral route using the pharmaceutical composition of the present invention. Dosages will generally range, based on body weight, from about 0.01 mg/kg to about 50 mg/kg; from about 1 mg/kg to about 40 mg/kg; from about 5 mg/kg to about 30 mg/kg; from about 10 to about 25 mg/kg; about 10 mg/kg; about 20 mg/kg; about 25 mg/kg; about 30 mg/kg; etc.

Any suitable dosing interval can be used in accordance with the present invention. For example, DAST can be administered once, twice (BID), three, four, etc., times a day. For example, about 100, about 200, about 400 mg, about 500 mg, about 600 mg, or about 800 mg can be administered one, twice, or three times daily.

DAST can be administered at any suitable time. For example, it can be administered routinely as other chemotherapeutic agents; it can be administered as a bolus prior to a surgical intervention; prior to or after radiation, radiofrequency ablation and other energy treatments; post-operatively; pre-operatively; etc.

DAST can be further combined with any other suitable additive or pharmaceutically acceptable carrier. Such additives include any of those used conventionally, such as those described in Remington: The Science and Practice of Pharmacy (Gennaro and Gennaro, eds, 20th edition, Lippincott Williams & Wilkins, 2000); Theory and Practice of Industrial Pharmacy (Lachman et al., eds., 3rd edition, Lippincott Williams & Wilkins, 1986); Encyclopedia of Pharmaceutical Technology (Swarbrick and Boylan, eds., 2nd edition, Marcel Dekker, 2002).

DAST and the pharmaceutical compositions of the present invention can be in any suitable form, without limitation. Forms suitable for oral use, include, but are not limited to, tablets, troches, lozenges, aqueous or oily suspensions, dispersible powders or granules, emulsions, hard or soft capsules, solutions, syrups and elixirs. Compositions intended for oral use may be prepared according to any method known to the art for the manufacture of pharmaceutical compositions.

DAST can be formulated with other ingredients, e.g., "pharmaceutically acceptable carriers" or "excipients" to indicate they are combined with the active drug and can be administered safely to a subject for therapeutic purposes. These include, but are not limited to, antioxidants, preservatives, dyes, tablet-coating compositions, plasticizers, inert carriers, excipients, polymers, coating materials, osmotic barriers, devices and agents which slow or retard solubility, etc.

Pharmaceutical compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations.

Non-toxic pharmaceutically acceptable excipients that are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

DAST and the pharmaceutical compositions of the present invention may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

DAST and the pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

DAST and the pharmaceutical compositions of the invention may also be administered in the form of suppositories for rectal or vaginal administration of the drug. These compositions can be prepared by mixing the drug with a suitable non-irritating excipient which is solid at ordinary temperatures but liquid at the rectal temperature or vaginal temperature and will therefore melt in the rectum or vagina to release the drug. Such materials include cocoa butter and polyethylene glycols.

DAST and the pharmaceutical compositions of the invention may also be administrated transdermally using methods known to those skilled in the art (see, for example: Chien; "Transdermal Controlled Systemic Medications"; Marcel Dekker, Inc.; 1987. Lipp et al. WO94/04157). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates may also be used as matrix components. Additional additives, such as viscous resins or oils may be added to increase the viscosity of the matrix.

Compositions comprising precursors can also be formulated for controlled release, where release of the active ingredient is regulated or modulated to achieve a desired rate of delivery into the systemic circulation. A controlled release formulation can be pulsed, delayed, extended, slow, steady, immediate, rapid, fast, etc. It can comprise one or more release formulations, e.g. extended- and immediate-release components. Extended delivery systems can be utilized to achieve a dosing internal of once every 24 hours, once every 12 hours, once every 8 hours, once every 6 hours, etc. The dosage form/delivery system can be a tablet or a capsule suited for extended release, but a sustained release liquid or suspension can also be used. A controlled release pharmaceutical formulation can be produced which maintains the release of, and or peak blood plasma levels of DAST.

In preferred solid oral pharmaceutical compositions according to the invention, at least 25% of DAST exists as a coprecipitate, more preferable at least 40% of DAST exists as a coprecipitate.

Micronization can be achieved by standard milling methods, preferably by air chat milling, known to a skilled person. The micronized form can have a mean particle size of from 0.5 to 10 μm, preferably from 1 to 6 μm, more preferably from 1 to 3 μm. The indicated particle size is the mean of the particle size distribution measured by laser diffraction known to a skilled person (measuring device: HELOS, Sympatec).

Pharmaceutical compositions which are preferred comprise DAST in a portion of at least 25%, preferably at least 45%, more preferably at least 50%, even more preferably at least 55%, by weight of the composition. Amounts of at least 62%, or at least 69%, or at least 75% by weight of the composition can be used under certain circumstances. Methods for preparing such formulations are disclosed in published international applications WO05/009961, published Feb. 3, 2005, and WO06/026500, published Mar. 9, 2006, which are incorporated herein by reference.

Without further elaboration, it is believed that one skilled in the art, using the preceding description, can utilize the present invention to its fullest extent. The following preferred specific embodiments are, therefore, to be construed as merely illustrative, and not limitative of the remainder of the disclosure in any way whatsoever. The entire disclosure of all applications, patents and publications, cited above and in the figures are hereby incorporated by reference in their entirety.

BIOLOGICAL EXAMPLES

Generation of c-KIT-Expressing Ba/F3 Cell Lines

The cDNA encoding full length human c-KIT with a deletion in exon 11 that removed amino acid residues 557-558 was ligated into the mammalian expression vector pClneo (Promega). Imatinib (Gleevec)-resistant variants of the KIT exon 11 deletion mutant were generated. All mutations were confirmed by DNA sequencing.

The expression vectors encoding the c-KIT exon 11 mutant or its Imatinib (Gleevec)-resistant mutant variants were transfected into Ba/F3 cells by electroporation. Selective pressure was applied to the transfected cells by removing IL-3 from the culture medium. After IL-independent populations, further selective pressure was applied by also growing the cells in the presence of 1 mg/mL G418. The resulting stable pools of Ba/F3 cells were found to express c-KIT by western blot using an antibody specific for c-KIT. The stable pools were further characterized by sequencing genomic DNA to confirm the presence of the transfected c-KIT cDNA.

Cell Proliferation Assay

This assay utilizes cellular ATP as a marker for cell proliferation/viability. On day 1, Ba/F3 cells were plated in 96 well dishes (Costar 3603) at 10,000 cells per well in 10% FBS in RPMI medium with 1 mg/ml G418. Test compounds, serially diluted in the same medium at 10× for an eight-point dose response to give rise to final concentrations ranging from 0.6 to 10,000 nM, were added to the cells. Plates were then incubated in a 5% CO2 incubator at 37° C. for 3 days. After 72 h, 100 microliters of lysis/luciferase reagent (CellTiter-Glo, Promega G7573) was added to each well. The cells were then incubated on a shaker for 5 minutes at room temperature, and luminescence was measured on a Victor 5 (Perkin Elmer) spectrophotometer. Growth inhibition was measured by comparing luminescence signal from treated vs. untreated cells in assay plates, and the IC50 analysis of cell proliferation inhibition by compounds was analyzed using Analyze 5 in-house software. IC50 values obtained for Imatinib (Gleevec) and Nexavar in the various c-KIT-expressing Ba/F3 cell lines are summarized in Table 1. The IC50 values are mean values calculated from at least three experiments.

TABLE 1

Average IC$_{50}$ [nM] for c-KIT-expressing Ba/F3 cellular proliferation, n ≥ 3
c-KIT Cytoplasmic Domain

| Inhibitor | Exon 11 Deletion | Exon 11 + V654A | Exon 11 + T670I | Exon 11 + D816G | Exon 11 + N822K | Exon 11 + Y823D |
|---|---|---|---|---|---|---|
| Imatinib (Gleevec) | 5 | 168 | >10,000 | 87 | 221 | 295 |
| DAST | 7 | 38 | 19 | 14 | 12 | 129* |

TABLE 2

(SEQ ID NO: 1)

| K | P | M | Y | E | V | Q | W | K | V | V | E | E | I | N | G |
|---|---|---|---|---|---|---|---|---|---|---|---|---|---|---|---|
| 50 | 51 | 52 | 53 | 54 | 55 | 56 | 57 | 58 | 59 | 60 | 61 | 62 | 63 | 64 | 65 |

TABLE 2-continued

| N | N | Y | V | Y | I | D | P | T | Q | L | P | Y | D | H |
|---|---|---|---|---|---|---|---|---|---|---|---|---|---|---|
| 66 | 67 | 68 | 69 | 70 | 71 | 72 | 73 | 74 | 75 | 76 | 77 | 78 | 79 | 80 |

---

What is claimed is:

1. A method of treating a cancer in a subject in need thereof, wherein said cancer was initially sensitive to KIT tyrosine kinase inhibitor and acquired resistance to said KIT tyrosine kinase inhibitor, said method comprising:
   administering to said subject, an effective amount of 4{4-[3-(4-chloro-3-trifluoromethylphenyl)-ureido]-3-fluorophenoxy}-pyridine-2-carboxylic acid methylamide of the formula I below including all polymorphs, hydrates, pharmaceutically acceptable salts, metabolites, prodrugs, solvates or combinations thereof.

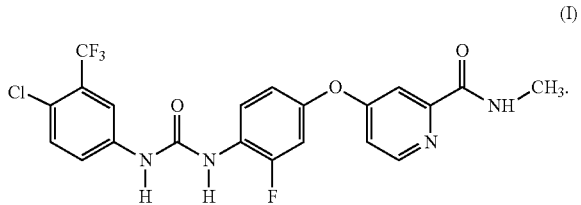 [SMILES: CNC(=O)c1cc(Oc2ccc(NC(=O)Nc3ccc(Cl)c(C(F)(F)F)c3)c(F)c2)ccn1]

(I)

2. A method as in claim 1 wherein the cancer has acquired resistance to one of the following KIT inhibitors:
   imatinib mesylate, salts of imatinib mesylate; PP1(4-Amino-5-(4-methylphenyl)-7-(t-butyl)pyrazolo[3,4-d]pyrimidine); MLN518 (CT53518); PD180970; SU112481 SU5416; SU5414; SU6597; SU6663 or SU6561.

3. A method as in claim 1 wherein said cancer is one or more of a malignant gastrointestinal stromal tumor (GIST), a benign gastrointestinal stromal tumor (GIST), a mesenchymal tumor of the intestinal tract, chronic myelogenous leukemia (CML), a mast cell tumor, SCLC, a germ cell tumors, breast cancer, and/or neuroblastoma.

4. A method as in claim 1 wherein the cancer has acquired resistance to imatinib mesylate.

5. A method of claim 1, wherein said acquired resistance of said cancer is associated with a secondary mutation in a KIT gene mutated in the primary tumor.

6. A method of claim 5, wherein said secondary mutation is in the kinase catalytic domain.

7. A method as in aspect claim 5 wherein the mutation is in Exons 13, 14, and or 17.

8. A method as in claim 5 wherein the mutation is at residues 654, 670, 716.816, 820, 822, and 823.

9. A method as in claim 5 wherein the mutation is at residues 650-654.

10. A method as in claim 5 wherein the mutation is at residues 670-674.

11. A method as in claim 5 wherein the mutation is at residues 816-824.

12. A method as in claim 5 wherein the secondary mutation is one or more of V654A (Exon 13), T670I (Exon 14), T670E, D716N, S709F (Exon 14), D816G, D816E (Exon 17), D820E, D820Y, D820G N822K, Y823D (Exon 17), or deletions and other amino acid substitutions at such positions or adjacent positions.

13. A method as in claim 5 wherein the secondary mutation is one or more of
   i) deletion of amino acid residues 557-558;
   ii) deletion of amino acid residues 551-555;
   iii) deletion of amino acid residues 550-558;
   iv) deletion of amino acid residues 559-560;
   v) deletion of amino acid residues 557-561;
   vi) deletion of amino acid residues 554-558;
   vii) deletion of amino acid residues 552-557;
   viii) mutations at residue 559, including V559D, V559A, or V559G;
   ix) mutations at residue 560, including V560D, V560E, or V560G;
   x) W557S, alone, or in combination with a deletion of amino acids 552-556;
   xi) mutations at amino acid residue 557, including W557R; and
   xii) mutations at amino acid residue 576, including L576P.

14. A method as in claim 5 wherein the secondary mutation is deletion of residues 557-558 and at least one of the following mutations: V654A, T670I, D820Y, N822K, or Y823D.

15. A method of treating a cancer in a subject in need thereof said cancer having a primary and/or secondary KIT gene mutation in the primary tumor, said method comprising:
   administering to said subject, an effective amount of the compound 4{4-[3-(4-chloro-3-trifluoromethylphenyl)-ureido]-3-fluorophenoxy}-pyridine-2-carboxylic acid methylamide of the formula I below including all polymorphs, hydrates, pharmaceutically acceptable salts, metabolites, ester prodrugs, solvates or combinations thereof.

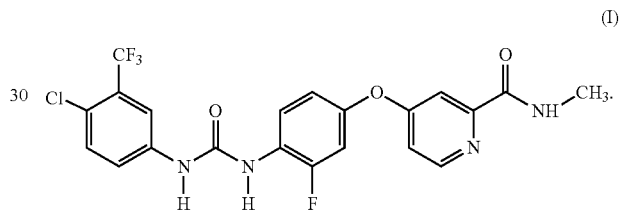

(I)

16. A method of claim 15, wherein said primary and/or secondary KIT gene mutation in the primary tumor is associated with acquired resistance of said cancer to KIT tyrosine kinase inhibitors.

17. A method of claim 15, wherein said secondary mutation is in the kinase catalytic domain.

18. A method as in claim 15 wherein the mutation is in Exons 13, 14, and or 17.

19. A method as in claim 15 wherein the mutation is at residues 654, 670, 716, 816, 820, 822, and 823.

20. A method as in claim 15 wherein the mutation is at residues 650-654.

21. A method as in claim 15 wherein the mutation is at residues 670-674.

22. A method as in claim 15 wherein the mutation is at residues 816-824.

23. A method as in claim 15 wherein the secondary mutation is one or more of V654A (Exon 13), T670I (Exon 14), T670E, D716N, S709F (Exon 14), D816G, D816E (Exon 17), D820E, D820Y, D820G N822K, Y823D (Exon 17), or deletions and other amino acid substitutions at such positions or adjacent positions.

24. A method as in claim 15 wherein the secondary mutation is one or more of
   i) deletion of amino acid residues 557-558;
   ii) deletion of amino acid residues 551-555;
   iii) deletion of amino acid residues 550-558;
   iv) deletion of amino acid residues 559-560;
   v) deletion of amino acid residues 557-561;
   vi) deletion of amino acid residues 554-558;
   vii) deletion of amino acid residues 552-557;

viii) mutations at residue 559, including V559D, V559A, or V559G;
ix) mutations at residue 560, including V560D, V560E, or V560G;
x) W557S, alone, or in combination with a deletion of amino acids 552-556;
xi) mutations at amino acid residue 557, including W557R; and
xii) mutations at amino acid residue 576, including L576P.

25. A method as in claim 15 wherein the secondary mutation is deletion of residues 557-558 and at least one of the following mutations: V654A, T670I, D820Y, N822K, or Y823D.

26. A method of treating a cancer in a subject in need thereof said cancer having a primary and/or secondary KIT gene mutation associated with resistance or acquired resistance to imatinib mesylate or salts of imatinib mesylate, said method comprising:
administering to said subject, an effective amount of the compound 4{4-[3-(4-chloro-3-trifluoromethylphenyl)-ureido]-3-fluorophenoxy}-pyridine-2-carboxylic acid methylamide of the formula I below including all polymorphs, hydrates, pharmaceutically acceptable salts, metabolites, ester prodrugs, solvates or combinations thereof.

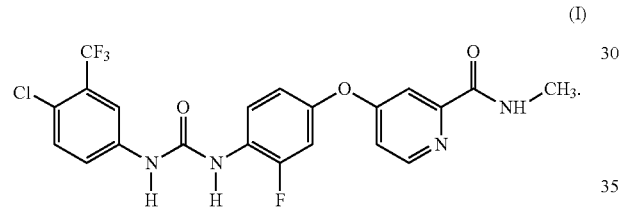

27. A method for treating cancer in a human subject with imatinib mesylate or salts of imatinib mesylate, which additionally comprises:
administering to said human subject, an effective amount of the compound 4{4-[3-(4-chloro-3-trifluoromethylphenyl)-ureido]-3-fluorophenoxy}-pyridine-2-carboxylic acid methylamide of the formula I below including all polymorphs, hydrates, pharmaceutically acceptable salts, metabolites, ester prodrugs, solvates or combinations thereof.

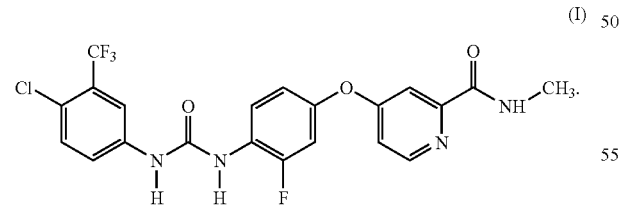

28. A method as in claim 1 wherein the cancer which is treated is:
Accelerated Phase Chronic Myelogenous Leukemia; Acute Erythroid Leukemia; Acute Lymphoblastic Leukemia; Acute Lymphoblastic Leukemia in Remission; Acute Lymphocytic Leukemia; Acute Monoblastic and Acute; Monocytic Leukemia; Acute Myelogenous Leukemia; Acute Myeloid Leukemia; Adenocarcinoma of the Prostate; Adenoid Cystic Carcinoma of the Head and Neck; Advanced Gastrointestinal Stromal Tumor; Agnogenic Myeloid; Metaplasia; Anaplastic Oligodendroglioma; Astrocytoma; B-Cell Adult Acute Lymphoblastic Leukemia; Blastic Phase Chronic Myelogenous Leukemia; Bone Metastases; Brain Tumor; Breast Cancer; Cancer; Central Nervous System Cancer; Childhood Acute Lymphoblastic Leukemia; Childhood Acute Lymphoblastic Leukemia in Remission; Childhood Central Nervous System Germ Cell Tumor; Childhood Chronic Myelogenous Leukemia; Childhood Soft Tissue Sarcoma; Chordoma; Chronic Eosinophilic Leukemia (CEL); Chronic Idiopathic Myelofibrosis; Chronic Myelogenous Leukemia; Chronic Myeloid Leukemia; Chronic Myelomonocytic Leukemia; Chronic Phase Chronic Myelogenous Leukemia; Colon Cancer; Colorectal Cancer; Dermatofibrosarcoma; Dermatofibrosarcoma Protuberans (DFSP); Desmoid Tumor; Eosinophilia; Epidemic Kaposi's Sarcoma; Essential Thrombocythemia; Ewing's Family of Tumors; Extensive Stage Small Cell Lung Cancer; Fallopian Tube Cancer; Familiar Hypereosinophilia; Fibrosarcoma; Gastric Adenocarcinoma; Gastrointestinal Neoplasm; Gastrointestinal Stromal Tumor; Glioblastoma; Glioma; Gliosarcoma; Grade I Meningioma; Grade II Meningioma; Grade BI Meningioma; Hematopoietic and Lymphoid Cancer; High-Grade Childhood Cerebral Astrocytoma; Hypereosinophilic Syndrome; Idiopathic Pulmonary Fibrosis; L1 Adult Acute Lymphoblastic Leukemia; L2 Adult Acute Lymphoblastic Leukemia; Leukemia, Lymphocytic, Acute L2; Leukemia, Myeloid, Chronic; Leukemia, Myeloid, Chronic Phase; Liver Dysfunction and Neoplasm; Lung Disease; Lymphoid Blastic Phase of Chronic Myeloid Leukemia; Male Breast Cancer; Malignant Fibrous Histiocytoma; Mastocytosis; Meningeal Hemangiopericytoma; Meningioma; Meningioma; Meningioma; Metastatic Cancer; Metastatic Solid Tumors; Myelofibrosis; Myeloid Leukemia, Chronic; Myeloid Leukemia, Chronic Accelerated-Phase; Myeloid Leukemia, Chronic, Chronic-Phase; Myeloid Metaplasia; Myeloproliferative Disorder (MPD) with Eosinophilia; Neuroblastoma; Non-T, Non-B Childhood Acute Lymphoblastic Leukemia; Oligodendroglioma; Osteosarcoma; Ovarian Germ Cell Tumor; Ovarian Low Malignant Potential Tumor; Ovarian Neoplasms; Pancreatic Cancer; Pelvic Neoplasms; Peritoneal Cavity Cancer; Peritoneal Neoplasms; Philadelphia Chromosome Positive Chronic Myelogenous Leukemia; Philadelphia Positive Acute Lymphoblastic Leukemia; Philadelphia Positive Chronic Myeloid Leukemia in Myeloid Blast Crisis; Polycythemia Vera; Pulmonary Fibrosis; Recurrent Adult Brain Tumor; Recurrent Adult Soft Tissue Sarcoma; Recurrent Breast Cancer; Recurrent Colon Cancer; Recurrent Esophageal Cancer; Recurrent Gastric Cancer; Recurrent Glioblastoma Multiforme (GBM); Recurrent Kaposi's Sarcoma; Recurrent Melanoma; Recurrent Merkel Cell Carcinoma; Recurrent Ovarian Epithelial Cancer; Recurrent Pancreatic Cancer; Recurrent Prostate Cancer; Recurrent Rectal Cancer; Recurrent Salivary Gland Cancer; Recurrent Small Cell Lung Cancer; Recurrent Tumors of the Ewing's Family; Recurrent Uterine Sarcoma;

Relapsing Chronic Myelogenous Leukemia; Rheumatoid Arthritis; Salivary Gland Adenoid Cystic Carcinoma; Sarcoma; Small Cell Lung Cancer; Stage II Melanoma; Stage II Merkel Cell Carcinoma; Stage III Adult Soft Tissue Sarcoma; Stage III Esophageal Cancer; Stage III Merkel Cell Carcinoma; Stage III Ovarian Epithelial Cancer; Stage III Pancreatic Cancer; Stage III Salivary Gland Cancer; Stage IIIB Breast Cancer; Stage IIIC Breast Cancer; Stage IV Adult Soft Tissue Sarcoma; Stage W Breast Cancer; Stage IV Colon Cancer; Stage IV Esophageal Cancer; Stage IV Gastric Cancer; Stage IV Melanoma; Stage IV Ovarian Epithelial Cancer; Stage IV Prostate Cancer; Stage IV Rectal Cancer; Stage IV Salivary Gland Cancer; Stage IVA Pancreatic Cancer; Stage IVB Pancreatic Cancer; Systemic Mastocytosis; T-Cell Childhood Acute Lymphoblastic Leukemia; Testicular Cancer; Thyroid Cancer; Unresectable or Metastatic Malignant Gastrointestinal Stromal Tumor (GIST); Unspecified Adult Solid Tumor; Untreated Childhood Brain Stem Glioma; Uterine Carcinosarcoma, and Uterine Sarcoma.

29. A method of treating a cancer in a subject who has acquired resistance to imatinib, comprising:

administering an effective amount of 4{4-[3-(4-chloro-3-trifluoromethylphenyl)-ureido]-3-fluorophenoxy}-pyridine-2-carboxylic acid methylamide of the formula I below including all polymorphs, hydrates, pharmaceutically acceptable salts, metabolites, prodrugs, solvates or combinations thereof, to said subject.

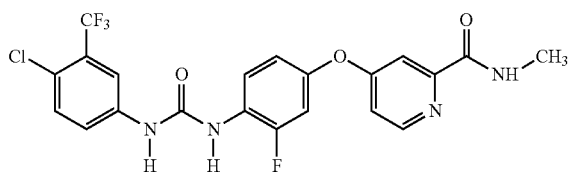

30. A method of treating a malignant gastrointestinal stromal tumor (GIST) or a benign gastrointestinal stromal tumor (GIST), in a subject who has been treated with imatinib, salts of imatinib mesylate, PP1(4-Amino-5-(4-methylphenyl)-7-(t-butyl)pyrazolo[3,4-d]pyrimidine); MLN518 (CT53518); PD180970; SU112481; SU5416; SU5414; SU6597; SU6663 or SU6561, said method comprising administering an effective amount of 4{4-[3-(4-chloro-3-trifluoromethylphenyl)-ureido]-3-fluorophenoxy}-pyridine-2-carboxylic acid methylamide of the formula I to said subject

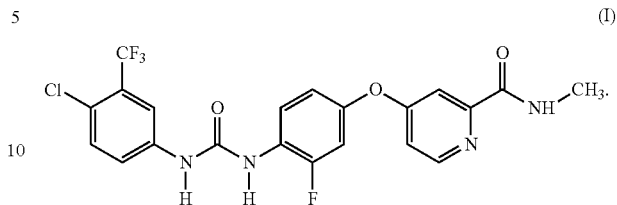

31. A method of treating a malignant gastrointestinal stromal tumor (GIST) or a benign gastrointestinal stromal tumor (GIST), in a subject who has been treated with imatinib, said method comprising administering an effective amount of 4{4-[3-(4-chloro-3-trifluoromethylphenyl)-ureido]-3-fluorophenoxy}-pyridine-2-carboxylic acid methylamide of the formula I to said subject

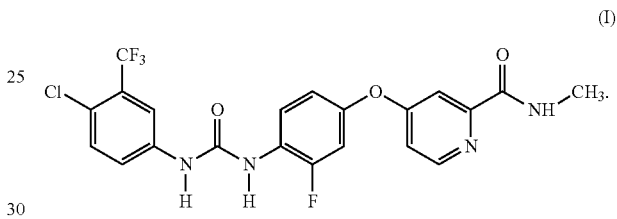

32. A method of treating a malignant gastrointestinal stromal tumor (GIST) or a benign gastrointestinal stromal tumor (GIST), said method comprising administering an effective amount of 4{4-[3-(4-chloro-3-trifluoromethylphenyl)-ureido]-3-fluorophenoxy}-pyridine-2-carboxylic acid methylamide of the formula I to said subject

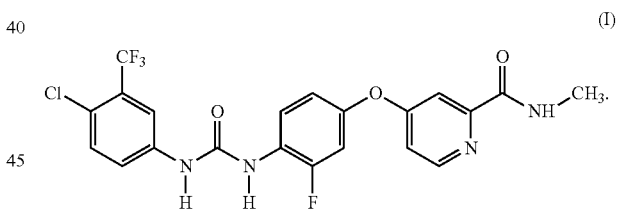

33. A method of claim 32 wherein said subject has not been treated with imatinib.

34. A method of claim 32 wherein said subject has not acquired resistance to cKit inhibitor.

* * * * *

UNITED STATES PATENT AND TRADEMARK OFFICE
CERTIFICATE OF CORRECTION

PATENT NO. : 8,680,124 B2
APPLICATION NO. : 12/523652
DATED : March 25, 2014
INVENTOR(S) : Wilhelm et al.

Page 1 of 1

It is certified that error appears in the above-identified patent and that said Letters Patent is hereby corrected as shown below:

In the Claims

Column 21, Line 44 reads: "7. A method as in aspect claim 5 wherein the mutation is in" should read --7. A method in claim 5 wherein the mutation is in--.

Column 24, Line 27 reads: "gioma; Grade BI Meningioma; Hematopoietic and" should read --gioma; Grade III Meningioma; Hematopoietic and--.

Column 25, Line 10 reads: "coma; Stage W Breast Cancer; Stage IV Colon Cancer;" should read --coma; Stage IV Breast Cancer; Stage IV Colon Cancer;--.

Signed and Sealed this
Fifth Day of August, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,680,124 B2 | Page 1 of 1 |
| APPLICATION NO. | : 12/523652 | |
| DATED | : March 25, 2014 | |
| INVENTOR(S) | : Wilhelm et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 866 days.

Signed and Sealed this
Ninth Day of June, 2015

Michelle K. Lee
*Director of the United States Patent and Trademark Office*

SEQUENCE LISTING

<160> NUMBER OF SEQ ID NOS: 1

<210> SEQ ID NO 1

<211> LENGTH: 31

<212> TYPE: PRT

<213> ORGANISM: Homo sapiens

<400> SEQUENCE: 1

```
Lys Pro Met Tyr Glu Val Gln Trp Lys Val Val Glu Glu Ile Asn Gly
1               5                   10                  15

Asn Asn Tyr Val Tyr Ile Asp Pro Thr Gln Leu Pro Tyr Asp His
            20                  25                  30
```